United States Patent
Schultheiss et al.

(10) Patent No.: US 10,280,132 B2
(45) Date of Patent: May 7, 2019

(54) PROCESS FOR CATALYTIC TRANSVINYLATION OF CARBOXYLIC ACIDS

(71) Applicant: Wacker Chemie AG, Munich (DE)

(72) Inventors: Peter Schultheiss, Burghausen (DE); Volker Hoellein, Burghausen (DE); Brigitte Patsch, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/537,231

(22) PCT Filed: Aug. 3, 2016

(86) PCT No.: PCT/EP2016/068521
§ 371 (c)(1),
(2) Date: Jun. 16, 2017

(87) PCT Pub. No.: WO2017/032572
PCT Pub. Date: Mar. 2, 2017

(65) Prior Publication Data
US 2018/0265448 A1   Sep. 20, 2018

(30) Foreign Application Priority Data

Aug. 27, 2015 (DE) .................. 10 2015 216 373

(51) Int. Cl.
*C07C 51/09* (2006.01)
*C07C 53/08* (2006.01)
(Continued)

(52) U.S. Cl.
CPC .............. *C07C 67/10* (2013.01); *C07C 51/09* (2013.01); *C07C 67/54* (2013.01); *Y02P 20/582* (2015.11)

(58) Field of Classification Search
CPC ................................ C07C 67/10; C07C 67/54
(Continued)

(56) References Cited

U.S. PATENT DOCUMENTS 4,981,973 A   1/1991  Murray
5,210,207 A   5/1993  Mokhtarzadeh et al.
(Continued)

FOREIGN PATENT DOCUMENTS

DE   102014206915 A1   10/2015
DE   102014206916 A1   10/2015
(Continued)

*Primary Examiner* — Deborah D Carr
(74) *Attorney, Agent, or Firm* — Brooks Kushman P.C.

(57) ABSTRACT

A carboxylic acid is transvinylated with vinyl ester to give a vinyl ester product and the corresponding acid of the vinyl ester in the presence of a catalyst, at a temperature of 100° C. to 170° C. and a pressure of 2 bar abs. to 15 bar abs., wherein the vinyl ester, the carboxylic acid and the catalyst are supplied to a reactor, the transvinylation reaction is conducted, and, on the completion of the transvinylation, the vinyl ester product is separated from the reaction mixture by distillation, characterized in that the reaction mixture is decompressed in a decompression vessel, the gaseous phase obtained is condensed and recycled into the reactor without further purification, and the liquid phase obtained is freed of vinyl ester and corresponding acid with a first distillation, and the vinyl ester product is separated from the reaction mixture in a further distillation step.

9 Claims, 1 Drawing Sheet

(51) Int. Cl.
   *C07C 67/10* (2006.01)
   *C07C 67/54* (2006.01)
   *C07C 69/01* (2006.01)
   *C07C 69/24* (2006.01)

(58) Field of Classification Search
   USPC .......................................................... 554/127
   See application file for complete search history.

(56) References Cited

U.S. PATENT DOCUMENTS

| | | |
|---|---|---|
| 2014/0343310 A1 | 11/2014 | Johnen et al. |
| 2014/0357881 A1 | 12/2014 | Johnen et al. |
| 2017/0036988 A1 | 2/2017 | Gigler et al. |

FOREIGN PATENT DOCUMENTS

| | | |
|---|---|---|
| WO | 9209554 A1 | 6/1992 |
| WO | 2011/139360 A1 | 11/2011 |
| WO | 2011/139361 A1 | 11/2011 |
| WO | 13117295 A1 | 8/2013 |
| WO | 2013117294 A1 | 8/2013 |
| WO | 2015078746 A1 | 6/2015 |
| WO | 2015078747 A1 | 6/2015 |

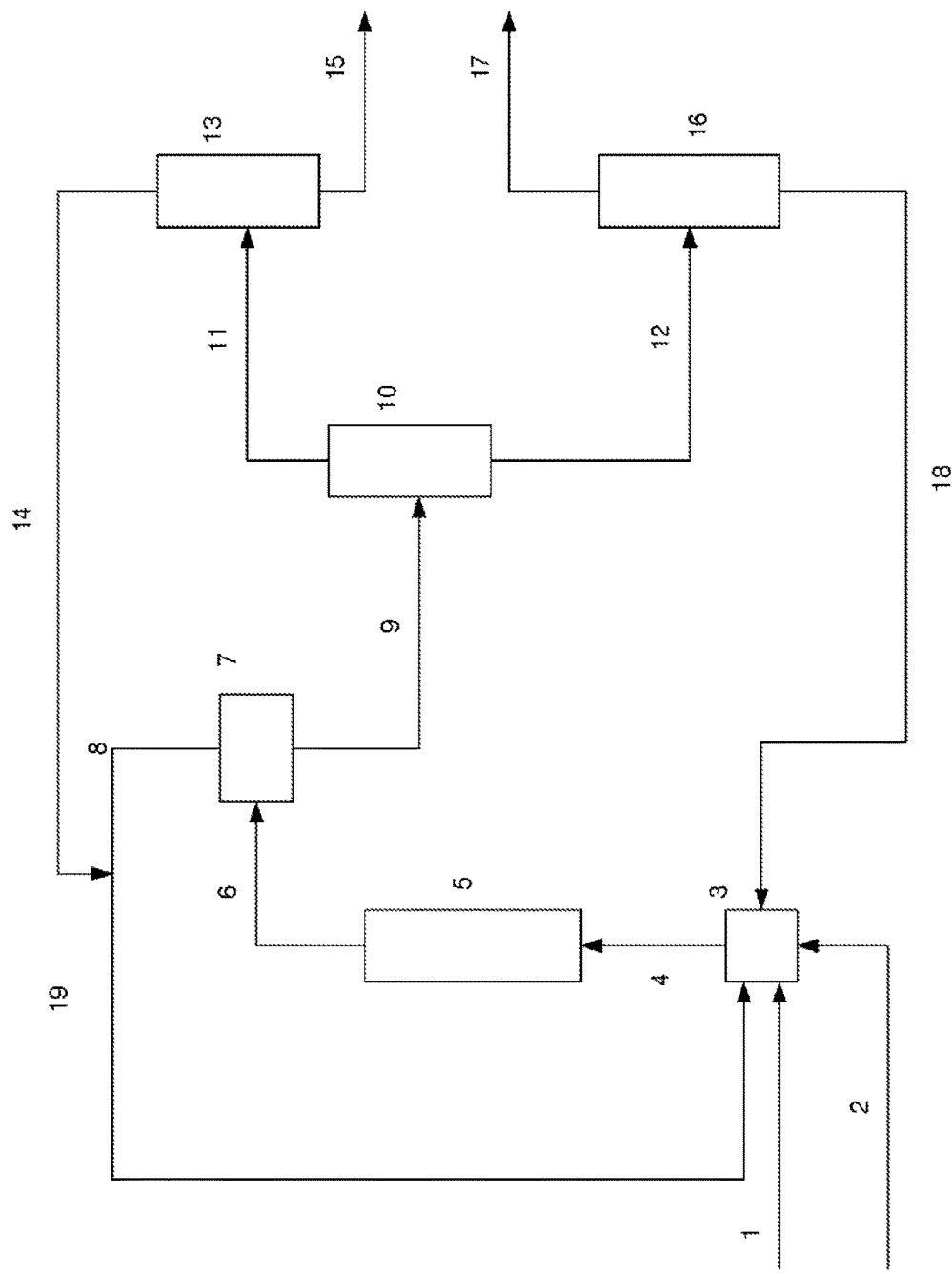

PROCESS FOR CATALYTIC TRANSVINYLATION OF CARBOXYLIC ACIDS

CROSS REFERENCE TO RELATED APPLICATIONS

This application is the U.S. National Phase of PCT Appln. No. PCT/EP2016/068521 filed Aug. 3, 2016, which claims priority to German Application No. 10 2015 216 373.3 filed Aug. 27, 2015, the disclosures of which are incorporated in their entirety by reference herein.

BACKGROUND OF THE INVENTION

1. Field of the Invention

The invention relates to a process for transvinylation of a carboxylic acid reactant with a vinyl ester reactant to give a vinyl ester product and the corresponding acid of the vinyl ester reactant in the presence of one or more catalysts, wherein the vinyl ester reactant, the carboxylic acid reactant and the catalyst are supplied to a reactor, the transvinylation reaction is conducted and, on completion of the transvinylation reaction, the product vinyl ester is separated by distillation.

2. Description of the Related Art

The transvinylation of carboxylic acids serves to produce vinyl esters. This is understood to mean the transfer of a vinyl unit of a vinyl ester reactant (1V) to a carboxylic acid reactant (2S) to generate a vinyl ester (2V) and the corresponding acid of the reactant vinyl ester reactant (1S).

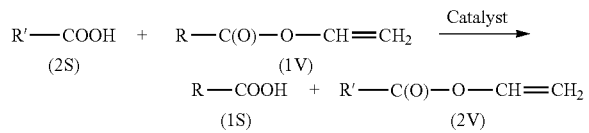

WO 92/09554 A1 describes a process for catalytic transvinylation in which, after the transvinylation, carboxylic acid reactant and catalyst are removed from the reaction mixture in a first step, and the vinyl ester product is then separated by means of azeotropic distillation after addition of water.

U.S. Pat. No. 5,210,207 describes a transvinylation process by means of reactive distillation, in which, to accelerate the reaction and to increase the selectivity thereof, at least one of the product components is removed from the reaction mixture.

WO 2011/139360 A1 describes a process for continuous catalytic transvinylation of a carboxylic acid with vinyl acetate to give a product vinyl ester and the corresponding acetic acid in a reactive distillation column in which, in order to shift the reaction equilibrium, a mixture of vinyl acetate and acetic acid is removed continuously from the reaction zone. The vinyl ester product is withdrawn from the column tray as a mixture still comprising catalyst and also carboxylic acid reactant and vinyl acetate. This mixture is liquefied in a condenser and the vinyl ester product is removed as a bottom product.

WO 2011/139361 A1 describes a process for semi-continuous catalytic transvinylation of a carboxylic acid with vinyl acetate to give a vinyl ester product and the corresponding acetic acid in a stirred reactor in which, in order to shift the reaction equilibrium, a mixture of vinyl acetate and acetic acid is removed continuously from the reaction zone. The vinyl ester product is withdrawn from the bottom of the stirred reactor as a mixture still comprising catalyst and also carboxylic acid reactant and vinyl acetate. This mixture is then separated by fractional distillation, wherein firstly vinyl acetate is distilled off, and after increasing pressure/temperature, the vinyl ester product is distilled off.

WO 2013/117294 A1 describes a continuous catalytic process for transvinylation of a carboxylic acid with a vinyl ester product to give a vinyl ester product and the corresponding acid. The reaction mixture is fed to a decompression vessel and depressurized to standard pressure therein. The reaction mixture is cooled prior to decompression in order to keep all components liquid as far as possible during the decompression. A gas phase optionally formed is passed into the second separating apparatus. The liquid reaction mixture is then separated in a first separating apparatus wherein a mixture of vinyl ester reactant, vinyl ester product and corresponding acid is removed at the top and is delivered to a second separating apparatus. In the second separating apparatus a mixture of vinyl ester product and corresponding acid is withdrawn at the bottom and fed to a third separating apparatus. The product vinyl ester precipitates in this as bottom product.

WO 2013/117295 A1 describes a continuous catalytic process for transvinylation of a carboxylic acid with a vinyl ester reactant to give a vinyl ester product and the corresponding acid, wherein the corresponding acid is derivatized in a final step. The reaction mixture is fed to a decompression vessel and depressurized to standard pressure therein, wherein the formation of a gas phase is suppressed by cooling. The liquid reaction mixture is then separated in a first separating apparatus wherein a mixture of vinyl ester reactant, vinyl ester product and corresponding acid is removed at the top and is delivered to a second separating apparatus. If a gas phase is formed during the decompression, this is also delivered to the second separating apparatus. In the second separating apparatus a mixture of vinyl ester product and corresponding acid is withdrawn at the bottom and fed to a third separating apparatus. The product vinyl ester precipitates in this apparatus as bottoms product. The acid obtained at the top is derivatized in a downstream process, for example, acetic acid can be reacted with ethylene and oxygen to give vinyl acetate.

WO 2015/078746 A1 and WO 2015/078747 A1 both describe a process for ruthenium-catalyzed transvinylation of a carboxylic acid with a vinyl ester reactant to give a vinyl ester product and the corresponding acid in which, on completion of the transvinylation reaction, the vinyl ester product and the corresponding acid are separated from the reaction mixture by distillation, the vinyl ester product is subsequently separated off by distillation and the remaining reaction mixture is fed back to the reactor.

Due to incomplete reaction during the transvinylation, vinyl ester reactant and carboxylic acid reactant remain in the reaction mixture and, in addition to the target vinyl ester product, the corresponding acid is still released from the vinyl ester reactant. Therefore, in the processes from the prior art, the reaction mixture formed in the transvinylation is usually divided in multi-stage distillation processes into its constituents and the vinyl ester product is isolated. In addition to the apparatus outlay, these separation processes are time-consuming and require a high energy expenditure.

The object consisted therefore of providing a process for catalytic transvinylation of carboxylic acids with which the product vinyl ester is accessible with low complexity but nevertheless with a high degree of purity.

SUMMARY OF THE INVENTION

The invention relates to a process for transvinylation of a carboxylic acid reactant with a vinyl ester reactant to give a vinyl ester product and the corresponding acid of the vinyl ester reactant in the presence of one or more catalysts, in a reactor at a temperature of 100° C. to 170° C. and a pressure of 2 bar abs. to 15 bar abs., wherein the vinyl ester reactant, the carboxylic acid reactant and the catalyst are supplied to a reactor, the transvinylation reaction is conducted and, on completion of the transvinylation reaction, the vinyl ester product is separated from the reaction mixture by distillation, characterized in that the reaction mixture is decompressed in a decompression vessel, the gaseous phase obtained is then condensed and recycled into the reactor without further purification, and the liquid phase obtained is freed of vinyl ester reactant and corresponding acid in a first distillation, and the vinyl ester product is separated from the reaction mixture in a further distillation step.

BRIEF DESCRIPTION OF THE DRAWINGS

FIG. 1 illustrates one embodiment of the invention.

DETAILED DESCRIPTION OF THE PREFERRED EMBODIMENTS

Any carboxylic vinyl ester of the general formula R—C(O)—O—CH=CH$_2$ may be used as a vinyl ester reactant, where R can be an aliphatic residue having 1 to 12 carbon atoms, a cycloaliphatic residue having up to 12 carbon atoms, or an aromatic residue having up to 12 carbon atoms. Preference is given to using low molecular weight vinyl esters reactants where R is an alkyl residue having 1 to 6 carbon atoms. Particular preference is given to using vinyl acetate.

Furthermore, at least one carboxylic acid reactant of the general formula R'—COOH is fed back to the reactor, where R' can be an aliphatic residue having 1 to 22 carbon atoms, a cycloaliphatic residue having up to 22 carbon atoms, an aromatic residue having up to 22 carbon atoms. Preference is given to using carboxylic acids reactants of the compound classes mentioned having 6 to 18 carbon atoms. Examples of these are caproic acid, cyclohexanecarboxylic acid, n-heptanoic acid, 2-methylhexanoic acid, 2-ethylhexanoic acid, n-octanoic acid, n-nonanoic acid, isononanoic acid, neo-nonanoic acid, n-decanoic acid, neodecanoic acid, lauric acid, myristic acid, palmitic acid, stearic acid, benzoic acid and naphthalenecarboxylic acid. Particular preference is given to versatic acidsR (alpha-branched carboxylic acids having 9 to 12 carbon atoms from Momentive) or neo acids having 9 to 12 carbon atoms, and fatty acids such as lauric acid, myristic acid, palmitic acid and stearic acid.

As catalysts, preference is given to Ru compounds or Pd compounds which are typically used for transvinylation reactions. Suitable catalysts are known to those skilled in the art, for example from WO 2011/139360 A1, WO 2011/139361 A1 and the U.S. Pat. No. 4,981,973, the disclosure of which is incorporated here by way of reference. Preference is given to using Ru compounds. Particularly preferred is the use of Ru acetate or an active Ru catalyst solution, which are known to those skilled in the art from the German published specifications DE 102014206915 and DE 102014206916.

The noble metal catalyst is typically used at concentrations of 0.1 to 10 000 ppm (noble metal content based on the reaction mass of vinyl ester reactant and carboxylic acid reactant), preference being given to the use of 1 to 1000 ppm (noble metal content based on the reaction mass of vinyl ester reactant and carboxylic acid reactant).

Optionally, a polymerization inhibitor can be added to the reactants. Preference is given to using 100 to 10,000 ppm of polymerization inhibitor, based on the reaction mass of vinyl ester reactant and carboxylic acid reactant. Examples of polymerization inhibitors are hydroquinone, methoxyhydroquinone, tertiary-butyl catechol, phenothiazine (PIZ) or nitroxide radicals such as TEMPO or 4-OH-TEMPO (TEMPO=2,2,6,6-tetramethylpiperidinyloxyl). Preference is given to the use of phenothiazine or hydroquinone.

For the transvinylation, the vinyl ester reactant, carboxylic acid reactant and catalyst reactants, and also optionally inhibitor, can be supplied to the reactor individually or as a mixture.

The molar ratio of vinyl ester reactant to carboxylic acid reactant can be from 1:10 to 10:1. Preference is given to a ratio of vinyl ester reactant to carboxylic acid reactant of 2:1 to 8:1, particular preference being given to a ratio of 3:1 to 6:1.

The fundamental operation of the process according to the invention is shown in FIG. 1:

The reactant streams of vinyl ester reactant (1) and carboxylic acid reactant (2), and also the recirculation streams (18 and 19) are optionally fed to an upstream mixer (3) and then (4) to the reactor (5), or fed directly to the reactor (5) in which the transvinylation takes place.

The transvinylation is generally carried out at a temperature of 100° C. to 170° C., preferably at a temperature of 120° C. to 150° C. The pressure at which the transvinylation is conducted is dependent on the temperature and is generally 2 bar abs. to 15 bar abs., preferably 5 bar abs. to 15 bar abs., and most preferably 5 bar abs. to 10 bar abs. . . . The reaction is preferably conducted in a protective gas atmosphere, nitrogen for example, in a manner known per se. The transvinylation is carried out without reactive distillation.

Stirred tank reactors, stirred tank reactor cascades, or tubular reactors may be used as reactor (5). Reactor (5) is preferably a tubular reactor. A mixer (3) can optionally be connected upstream of the reactor (5) in which the reactants may be pre-mixed. Suitable mixers are static mixers or dynamic mixers, wherein static mixers are preferred.

The residence time in the reactor in the process according to the invention is generally 0.25 to 5 hours, preferably 1 hour to 4 hours.

The reaction mixture (6) obtained in the transvinylation is withdrawn continuously or batchwise from the reactor and depressurized in a decompression vessel (7). In general, the mixture is depressurized to a pressure from 0.5 bar abs. to 1.5 bar abs. Preferably, the mixture is depressurized to standard pressure (1 bar abs.). Suitable decompression vessels are known to those skilled in the art and are commercially available, for example, under the name Flash Box.

During the decompression, a gaseous phase (vapor phase) is formed comprising predominantly unreacted vinyl ester reactant and corresponding acid, and a liquid phase is formed comprising predominantly vinyl ester product and low proportions of vinyl ester reactant and corresponding acid and also catalyst and polymeric by-products. After the decompression, the reaction mixture is generally 60% by weight to 90% by weight liquid, and 10% by weight to 40% by weight of a gaseous phase, based in each case on the total weight of the reaction mixture withdrawn.

The fraction present in gaseous form after the decompression (8) is removed from the decompression vessel and is subsequently cooled by means of a heat exchanger and condensed and, without further purification after condensation thereof, is optionally fed back into the reactor (5) via the upstream mixer (3).

The liquid phase present after the decompression (9) is separated by distillation. Pressure and temperature of the distillation and the design of the distillation columns depend on the components present in the product mixture and may be determined, for example, by means of routine experiments by those skilled in the art. No azeotropic distillation is carried out.

From the resulting liquid phase (9) after the decompression, the vinyl ester reactant and corresponding acid thereof still present in this phase (11) is removed in a distillation apparatus (10). The mixture obtained here is separated in a second distillation apparatus (13) into the vinyl ester reactant (14) and corresponding acid (15). Subsequently, the recovered vinyl ester reactant (14), optionally together with the condensed vapor phase from the decompression (8), are optionally fed back into the upstream mixer or directly into the reactor (5).

The bottom product (12) from the distillation apparatus (10) comprising vinyl ester product, carboxylic acid reactant, polymeric by-products, possibly anhydrides and catalyst, is fed to a further distillation apparatus (16). If the boiling point of the vinyl ester product is lower than that of the carboxylic acid reactant, the vinyl ester product is completely or partially separated off as top product (17) from the residual constituents. The remaining catalyst-containing residue (18) is then fed back into the reactor (5) or optionally via the upstream mixer (3).

If the boiling point of the vinyl ester product is higher than that of the carboxylic acid reactant, a mixture of vinyl ester product and carboxylic acid reactant is separated off as top product (17) from the catalyst-containing residue in the distillation apparatus (16). This mixture is then separated in a further distillation apparatus to produce the pure vinyl ester product.

In contrast to the processes of the prior art, the entire reaction mixture resulting from the transvinylation is not separated by distillation in the present process but only the part which is obtained in the liquid phase after the decompression step. The vapor phase, in general 10 to 40% by weight of the reaction mixture withdrawn, is fed back without further work-up into the reactor.

With this measure, the expenditure for the distillation is significantly reduced, that is the capital costs and operating costs are significantly reduced. As the examples below show, the yields are not negatively affected despite this recycling.

In the processes of the prior art, the continuous distillations are conducted such that the vinyl ester product is obtained in the distillation as bottom product. In the present process, all lower-boiling constituents, generally the vinyl ester reactant and the corresponding acid, are removed from the mixture in the first step. If the boiling point of the vinyl ester product is lower than that of the carboxylic acid reactant, which is the case in almost all transvinylations carried out industrially, the vinyl ester product of the carboxylic acid reactant and the polymeric by-products can thus be obtained as top product in the distillation in the following distillation step and are therefore obtained with high purity.

The following examples serve to further illustrate the invention:

The Ru catalyst used in each case was 100 ppm [Ru$_3$O(OAc)$_6$(H$_2$O)$_3$]OAc in the form of an acetic acid solution with 4.5% by weight Ru from Umicore.

COMPARATIVE EXAMPLE 1

In a continuously operated tubular reactor, 25 kg/h of vinyl acetate, 6 kg/h of lauric acid and 30 kg/h of recirculated lauric acid, which still contained a mixture of lauric acid and lauric anhydride in addition to Ru catalyst, polymeric by-products and vinyl laurate, were metered into the reactor. The molar ratio of vinyl acetate and lauric acid was 4:1.

The reaction was carried out at 140° C. and 7 bar abs. Reaction mixture was continuously withdrawn and depressurized to atmospheric pressure. In this case, about 20% by weight of the reaction mixture withdrawn was obtained as a vapor phase with ca. 96% by weight vinyl acetate and ca. 4% by weight acetic acid, and also traces of vinyl laurate and lauric acid in the mixture. The stream generated by decompression was dispensed with on recirculation.

At an operating time of ca. 1000 hours, the yield fluctuated, depending on the polymer content and catalyst content, between 60% and 75%.

From the liquid phase obtained after decompression, a mixture of vinyl acetate and acetic acid was removed at the top in the first distillation, which was separated in a further distillation step. The bottom product of the first distillation was subjected to a further distillation. The vinyl laurate target product could be produced therefrom as top product with a purity of >99.0% by weight and without polymeric constituents.

EXAMPLE 2

In a continuously operated tubular reactor, 14 kg/h of vinyl acetate, 6 kg/h of lauric acid and 30 kg/h of recirculated lauric acid, which still contained a mixture of lauric acid and lauric anhydride in addition to Ru catalyst, polymeric by-products and vinyl laurate, and 12 kg/h of the gas phase as condensate obtained after decompressing the reaction mixture, were metered into the reactor. The molar ratio of vinyl acetate and lauric acid was 4:1.

The reaction was carried out at 140° C. and 7 bar abs. Reaction mixture was continuously withdrawn and depressurized to atmospheric pressure. In this case, about 20% by weight of the reaction mixture withdrawn was obtained as a vapor phase with ca. 96% by weight vinyl acetate and ca. 4% by weight acetic acid, and also traces of vinyl laurate and lauric acid. This vapor phase was separated off, compressed and fed back into the reactor as a condensate.

At an operating time of ca. 1000 hours, the yield fluctuated, depending on the polymer content and catalyst content, between 60% and 75%

From the liquid phase obtained after decompression, a mixture of vinyl acetate and acetic acid was removed at the top in the first distillation, which was separated in a further distillation step. The bottom product of the first distillation was subjected to a further distillation. The vinyl laurate target product could be produced therefrom as top product with a purity of >99.0% by weight and without polymeric constituents.

COMPARATIVE EXAMPLE 3

In a continuously operated tubular reactor, 30 kg/h of vinyl acetate, 7 kg/h of neodecanoic acid and 23 kg/h of recirculated neodecanoic acid, which still contained neodecanoic acid in addition to Ru catalyst and polymeric by-products and vinyl neodecanoate, were metered into the reactor. The gas phase generated by decompression was dispensed with here on recirculation. The molar ratio of vinyl acetate and neodecanoic acid was 4:1.

The reaction was carried out at 140° C. and 7 bar abs. Reaction mixture was continuously withdrawn and depressurized to atmospheric pressure. In this case, about 20% by weight of the reaction mixture withdrawn was obtained as a vapor phase which was not recirculated. The vapor phase comprised 92% by weight vinyl acetate, 6% by weight acetic acid, 1.5% by weight vinyl neodecanoate and 0.5% by weight neodecanoic acid.

At an operating time of ca. 1000 hours, the yield, depending on the polymer content and catalyst content, was between 45% and 75%.

From the liquid phase obtained after decompression, a mixture of vinyl acetate and acetic acid was removed at the top in the first distillation, which was separated in a further distillation step. The bottom product of the first distillation was subjected to a further distillation. The vinyl neodecanoate target product could be produced therefrom as top product with a purity of >99.0% by weight and without polymeric constituents.

EXAMPLE 4

In a continuously operated tubular reactor, 19 kg/h of vinyl acetate, 7 kg/h of neodecanoic acid, 23 kg/h of recirculated neodecanoic acid, which still contained polymeric by-products and vinyl neodecanoate and neodecanoic acid in addition to Ru catalyst, and 12 kg/h of the vapor phase obtained after decompression (in condensed form), were metered into the reactor. The molar ratio of vinyl acetate and neodecanoic acid was also 4:1.

The reaction was carried out at 140° C. and 7 bar abs. Reaction mixture was continuously withdrawn and depressurized to atmospheric pressure. In this case, about 20% by weight of the reaction mixture withdrawn was obtained as a vapor phase comprising 92% by weight vinyl acetate and 6% acetic acid, 1.5% vinyl neodecanoate and 0.5% neodecanoic acid. This vapor phase was separated off, cooled and fed back into the reactor as a condensate.

At an operating time of 1000 hours, the yield, depending on the polymer content and catalyst content, was between 60% and 75%

From the liquid phase obtained after decompression, a mixture of vinyl acetate and acetic acid was removed at the top in the first distillation, which was separated in a further distillation step. The bottom product of the first distillation was subjected to a further distillation. The vinyl neodecanoate target product could be produced as top product with a purity of >99.0% by weight and without polymeric constituents.

Comparison of example 2 with comparative example 1 or of example 4 with comparative example 3 shows that, with the process according to the invention, recycling of the gas phase obtained on decompression is possible without the quality or the yield being decreased. The savings resulting from recycling the gas phase can be achieved without reducing quality and yield.

The invention claimed is:

1. A process for the transvinylation of a carboxylic acid reactant with a vinyl ester reactant to give a vinyl ester product and a corresponding acid of the vinyl ester reactant, in the presence of one or more catalysts, comprising:
supplying, in a reactor, the vinyl ester reactant, the carboxylic acid reactant, and the catalyst, at a temperature of 100° C. to 170° C. and a pressure of 2 bar abs. to 15 bar abs. and conducting a transvinylation reaction, followed by separating the vinyl ester product from the reaction mixture by distillation, decompressing the reaction mixture in a decompression vessel, condensing a gaseous phase obtained thereby, and recycling the gaseous phase into the reactor without further purification, freeing vinyl ester reactant and corresponding acid in a first distillation, from a liquid phase obtained, and separating vinyl ester product from the reaction mixture in a further distillation.

2. The process of claim 1, wherein in the further distillation, the vinyl ester product is separated as a top product from residual constituents when the boiling point of the vinyl ester product is lower than the boiling point of the carboxylic acid reactant.

3. The process of claim 1, wherein in the further distillation step, when the boiling point of the vinyl ester product is higher than the boiling point of the carboxylic acid reactant, a mixture of vinyl ester product and carboxylic acid reactant is initially removed as a top product from a catalyst-containing residue, and this mixture is then separated in a subsequent distillation to obtain pure vinyl ester product.

4. The process of claim 1, wherein a carboxylic acid vinyl ester of the formula R—C(O)—O—CH=$CH_2$ is employed as vinyl ester reactant, where R is an aliphatic residue having 1 to 12 carbon atoms, or is a cycloaliphatic residue having up to 12 carbon atoms, or is an aromatic residue having up to 12 carbon atoms.

5. The process of claim 1, wherein vinyl acetate is employed as the vinyl ester reactant.

6. The process of claim 1, wherein a carboxylic acid of the formula R'—COOH is employed as carboxylic acid reactant, where R' is an aliphatic residue having 1 to 22 carbon atoms, or is a cycloaliphatic residue having up to 22 carbon atoms, or is an aromatic residue having up to 22 carbon atoms.

7. The process of claim 1, wherein the carboxylic acid reactant employed comprises a carboxylic acid selected from the group consisting of versatic acids and neo acids containing 9 to 12 carbon atoms, and fatty acids.

8. The process of claim 7, wherein the fatty acid comprises one of lauric acid, myristic acid, palmitic acid and stearic acid.

9. The process of claim 1, wherein the carboxylic acid reactant comprises a carboxylic acid whose boiling point is higher than the boiling point of the vinyl ester product.

* * * * *